United States Patent

Geller et al.

Patent Number: 5,283,067
Date of Patent: Feb. 1, 1994

[54] PARENTERAL SUSPENSIONS

[75] Inventors: Leo Geller, Riehen; Peter Glanzmann, Basle, both of Switzerland

[73] Assignee: Ciba-Geigy Corporation, Ardsley, N.Y.

[21] Appl. No.: 17,366

[22] Filed: Feb. 11, 1993

Related U.S. Application Data

[63] Continuation of Ser. No. 829,515, Jan. 31, 1992, abandoned, which is a continuation of Ser. No. 649,277, Jan. 30, 1991, abandoned, which is a continuation of Ser. No. 388,545, Aug. 1, 1989, abandoned.

[30] Foreign Application Priority Data

Jan. 30, 1987 [CH] Switzerland ............... 350/87-4

[51] Int. Cl.⁵ .......................... A61K 9/14; A61K 31/19
[52] U.S. Cl. .................... 424/489; 424/450; 514/561; 514/567
[58] Field of Search .......... 514/538, 561, 567, 886, 514/887

[56] References Cited

U.S. PATENT DOCUMENTS

| | | | |
|---|---|---|---|
| 3,973,024 | 8/1976 | Haas et al. | 424/263 |
| 4,309,421 | 1/1982 | Ghyczy et al. | 424/199 |
| 4,332,795 | 6/1982 | Ghyczy et al. | 424/199 |
| 4,378,354 | 3/1983 | Ghyczy et al. | 424/199 |
| 4,593,044 | 6/1986 | Metz | 514/557 |
| 4,614,741 | 9/1986 | Dell et al. | 514/222 |
| 4,711,906 | 12/1987 | Van Stetten et al. | 514/561 |
| 4,880,634 | 1/1989 | Speizer | 424/450 |

FOREIGN PATENT DOCUMENTS

| | | |
|---|---|---|
| 236855 | 9/1987 | European Pat. Off. |
| 1373913 | 12/1971 | United Kingdom |
| 2166651 | 5/1986 | United Kingdom |

OTHER PUBLICATIONS

Chem. Abstract of EP 181,121.
Chem. Abstract of EP 236,855.
Chem. Abstract of EP 152,379.

Primary Examiner—Thurman K. Page
Assistant Examiner—Neil Levy
Attorney, Agent, or Firm—Irving M. Fishman; Karen G. Kaiser; Barbara J. Ikeler

[57] ABSTRACT

The invention relates to a dry formulation, in particular a dry formulation obtainable by lyophilisation, which is suitable for the preparation of a stable, aqueous suspension for the parenteral administration of a diclofenac salt. The dry formulation contains a pharmaceutically acceptable and micronised salt of diclofenac and optional pharmaceutically acceptable adjuvants.

2 Claims, No Drawings

PARENTERAL SUSPENSIONS

This application is a continuation of application Ser. No. 07/829,515, filed Jan. 31, 1992 now abandoned, which application is a continuation of application Ser. No. 649,277, filed Jan. 30, 1991, now abandoned, which application is a continuation, of application Ser. No. 388,545, filed Aug. 1, 1989, now abandoned.

The present invention relates to a dry formulation, in particular a dry formulation obtainable by lyophilisation, which can be used for the preparation of an aqueous stable suspension for the parenteral administration of a diclofenac salt, to the use of said formulation for the preparation of a stable aqueous suspension containing said diclofenac salt, and to the use of this suspension in a therapeutic method of treating the human body.

Various medicaments of different structure are available for the treatment of inflammatory diseases, e.g. rheumatism. As the course inflammations take is often chronic, it is usually necessary to carry out the treatment with antiinflammatory drugs over a prolonged period of time without interruption. In particular, many non-steroidal antiinflammatory drugs (NAIDS), when administered orally, can cause disorders in the entire gastrointestinal tract, especially gastric ulcers.

The sodium salt of diclofenac, available under the registered trademark Voltaren ® (Ciba-Geigy), belongs to the group of non-steroidal antiinflammatory drugs of the first importance.

To enhance drug safety, there is a need to provide novel parenteral dosage forms for diclofenac and the salts thereof which, compared with the parenteral injection solutions of the known prior art disclosed e.g. in German Offenlegungsschrift 2 914 788 and European patent application 185 374, have the advantage of a very rapid onset of action with long-lasting therapeutic effects.

Suspensions of diclofenac or diclofenac sodium for parenteral, in particular intramuscular, administration are disclosed in U.S. Pat. No. 4,614,741. Fatty oils such as sesame oil, olive oil and the like, are used as suspending media for these suspensions. Quite generally, the use of fatty oils as adjuvants for parenteral dosage forms is inexpedient, as they increase the viscosity of the dosage form, thereby causing pain when it is administered (q.v. R. Voigt, Lehrbuch der Pharmazeutischen Technologie, Verlag Chemie, p. 383, 19.5.1.2.1). Consequently, there is also a need for suspensions containing a diclofenac salt, in particular diclofenac sodium, for substantially pain-free intramuscular administration.

The above objects of the invention are achieved by means of the present invention, which relates to a dry formulation containing a diclofenac salt in micronised form without deleterious adjuvants. This dry formulation, after being suspended in an aqueous liquid vehicle, is converted into a dosage form for parenteral administration.

Accordingly, the present invention relates to a dry formulation, in particular a dry formulation obtainable by lyophilisation, which can be used for the preparation of a stable aqueous suspension for the parenteral administration of a diclofenac salt. The dry formulation contains a pharmaceutically acceptable and micronised salt of diclofenac and optional pharmaceutically acceptable adjuvants.

A pharmaceutically acceptable salt of diclofenac, o-(2,6-dichloroanilino)phenylacetic acid, is in particular an alkali metal salt, e.g. the sodium or potassium salt, or a salt with an amine, e.g. a mono-, di- or trialkylamine containing 1 to 4 carbon atoms in the alkyl moiety or moieties, e.g. diethylamine or triethylamine, hydroxyalkylamine containing 2 to 4 carbon atoms in the alkyl moiety, e.g. ethanolamine, hydroxyalkylalkylamine containing 2 to 4 and 1 to 4 carbon atoms respectively in each of the alkyl moieties, e.g. dimethylethanolamine, or a quaternary ammonium salt, e.g. the tetramethylammonium salt or choline salt of diclofenac.

Particularly preferred salts of diclofenac are the sodium and potassium salts (q.v. Merck Index, Tenth Edition, No. 3066).

The dry formulation of this invention contains the diclofenac salt, in particular the sodium or potassium salt of diclofenac, in micronised form.

The micronised diclofenac salt has a preferred average particle size smaller than 50 $\mu$m, preferably smaller than 20 $\mu$m. Particles of this size are obtained by conventional comminution methods, e.g. grinding in an air jet mill, ball mill or vibrator mill. Micronisation is preferably effected by per se known methods using an ultrasonics disintegrator, e.g. of the Branson Sonifier type as described e.g. in J. Pharm. Sci. 53 (9), 1040–1045 (1965), or by stirring a suspension with a high-speed agitator, for example with a stirrer of the Homorex type (supplied by Brogli & Co., Basel). In these preferred methods, micronisation is effected at ca. 500 to 10,000 rpm by dissolving the appropriate salt of diclofenac in an organic solvent, e.g. methanol, ethanol or propylene glycol, and precipitating it in microcrystalline form at ca. 0°–5° C. in water or an aqueous salt solution, e.g. 2% sodium chloride solution which may additionally contain a protective colloid such as gelatin or a cellulose ether, e.g. methyl cellulose or hydroxypropyl methyl cellulose, in low concentration (0.1–1%), and filtering the resultant stirred suspension. The filter cake is dried at low temperature, e.g. ca. 0°–5° C., under vacuum (e.g. below 50 mbar, preferably at 0.5 mbar). The subsequent drying can be effected at ca. 50°–90° C.

Pharmaceutically acceptable adjuvants which the dry formulation may contain are e.g. ionic isotonic components such as sodium chloride, or nonionic components, especially builders, such as sorbitol, mannitol or glucose. Preferably the dry formulation contains these adjuvants, e.g. sodium chloride or mannitol, in the prescribed amounts which are necessary for establishing the isotonic conditions of the suspension.

Further adjuvants present in low concentration are e.g. emulsifiers which may be used as wetting agents, e.g. phospholipids, e.g. phosphatidyl choline (lecithin), phosphatidyl ethanolamine (cephalin), phosphatidyl serine, phosphatidyl inositol or mixtures of these lipids.

Preferred phospholipids are, for example, soybean or egg lecithin, or soybean or egg cephalin in pharmaceutical purity, or mixtures of phospholipids of different phosphatidyl choline content approved for pharmaceutical use, e.g. mixtures of lecithins which are commercially available under the registered trademarks Epikuron ® 145, 170 or 200 (Lucas Meyer, Hamburg) or Lipoid ® 45, 80 or 100 (Lipoid KG, Manneheim).

The cited phospholipids may be present in the solid formulation in weight ratios of active drug to phospholipid of 1:0.1 to 1:1, preferably from 1:0.1 to 1:1.

Further suitable adjuvants in the dry formulation are wetting agents useful for liquid pharmaceutical formulations or true surfactants, in particular nonionic surfactants of the fatty acid polyhydroxy alcohol ester type such as sorbitan monolaurate, monooleate, monostearate or monopalmitate, sorbitan tristearate or trioleate, adducts of polyoxyethylene and fatty acid polyhydroxy alcohol esters such as polyoxyethylene sorbitan monolaurate, monooleate, monostearate, monopalmitate, tristearate or trioleate, polyethylene glycol fatty acid esters such as polyoxyethyl stearate, polyethylene glycol 400 stearate, polyethylene glycol 2000 stearate, in particular ethylene oxide-propylene oxide block copolymers of the Pluronics® (Wyandotte) or Synperonic® (ICI).

These surfactants may be present in the dry formulation in weight ratios of active drug to surfactant of $1:1.0 \times 10^{-4}$ to $1:0.1$, preferably of $1:0.03$ to $1:0.1$.

The dry formulation of this invention is prepared by suspending the amount of diclofenac salt intended for parenteral administration, in micronised form, in a suspending medium that contains the optional pharmaceutically acceptable adjuvants, and removing the solvent.

If the dry formulation contains water-soluble components or adjuvants, such as sodium chloride, mannitol or glucose, which are necessary e.g. for establishing isotonic conditions, then an aqueous suspending medium is preferred. After dissolving the adjuvants in water purified for injection, the aqueous solution is preferably filtered and sterilized or filtered under sterile conditions. To this sterilized solution is then added the micronised diclofenac salt. The preparation of the dry formulation can be effected by known methods of lyophilisation, e.g. normally by filling a specific amount of the prepared suspension into suitable containers such as ampoules, e.g. vials, and thereafter freezing the filled vials at ca. $-40°$ to $-50°$ C., preferably at $-45°$ C., and then carrying out lyophilisation under a pressure of ca. 0.05 to 0.6 mbar by slowly warming to a final temperature of ca. $25°-55°$ C.

If the dry formulation contains an adjuvant or component which is poorly soluble in water, e.g. a phospholipid such as lecithin, then said adjuvant is dissolved e.g. in a purified organic solvent such as tert-butanol, methanol, ethanol or methylene chloride, and the micronised salt is suspended in this solution. After stripping off the organic solvent, the dry formulation coated with the adjuvant, such as a phospholipid, is filled in powder form into suitable containers, e.g. vials.

Surprisingly, by means of the process of this invention it is possible to prepare dry formulations, especially lyophilized formulations, and suspensions that can be reconstituted therefrom and which are stable and suitable for injection.

The use of the dry formulations obtainable by the process of this invention for the preparation of injection suspensions is also an object of this invention. These injection suspensions can be administered as injection formulations parenterally, preferably intramuscularly.

The dry formulation of this invention is reconstituted, prior to administration, as a suspension in the prescribed amount of liquid, especially sterilized (pyrogen-free) water for injection.

A homogeneous suspension of the previously micronised drug is formed once more by shaking. Instead of a dry formulation containing the diclofenac salt and the water-soluble adjuvants such as sodium chloride or mannitol, it is also possible to suspend a dry formulation containing only the diclofenac salt (without adjuvants) in the prescribed amount of liquid containing the cited water-soluble adjuvants.

The particle size of the micronised drug remains unchanged during the preparation of the suspension. Thus no noticeable crystal growth, e.g. resulting from hydrate formation, is observed in the suspension to be administered. The suspension of the drug also has the advantage that it does not adhere to the wall of the ampoule and can be readily and completely withdrawn from the ampoule with the syringe. A particularly preferred embodiment of the invention comprises preparing injection suspensions that contain the customary doses of 50, 75 or 100 mg of diclofenac sodium, having a total volume of 1.0 to 3.0 ml, preferably of 2.0–1.0 ml, especially a volume of 1.0 ml.

These suspensions can be used as ready for use formulations.

The present invention relates in particular to dry formulations and to the use thereof for the preparation of an aqueous suspension for the intramuscular administration of diclofenac sodium. The dry formulation and the suspension preferably contain micronised diclofenac sodium having an average particle size smaller than 20 $\mu$m and optional adjuvants such as sodium chloride, mannitol, sorbitol as well as lipids such as lecithin or wetting agents of the SYNPERONIC® or PLURONIC® type.

The suspensions of this invention can be used for parenteral (intramuscular) formulations for the treatment of painful conditions, inflammations and/or rheumatic diseases in warm-blooded animals (human and animals). Daily doses of ca. 25 to 200 mg of active drug can be administered, while the individual dosage form contains the customary amounts of drug of e.g. 25, 50, 75, 100 or 150 mg.

The following Examples illustrate the invention, but imply no restriction to what is described therein.

EXAMPLE 1 a) Preparation of the lyophilized drug formulation

| Composition of each ampoule: | |
|---|---|
| diclofenac sodium | 75 mg |
| NaCl | 18 mg |

Preparation of 10 ampoules:

180 mg of sodium chloride (puriss.) are dissolved in 10 ml of distilled water and the solution is filtered through a membrane filter (pore size: 0.2 $\mu$m) and sterilized, e.g. in an autoclave at ca. 120° C. The sterilized sodium chloride solution is cooled to 5° C. To the cooled solution are added 750 mg of micronised diclofenac sodium (puriss.) having an average particle size smaller than 20 $\mu$m and the resultant suspension is desagglomerated, e.g. in a piston homogeniser or ultrasonics disintegrator. the crystalline suspension is filled at 5° C. into 10 sterilized vials of 1.0 ml volume. The vials are frozen at $-45°$ C., lyophilized in a freeze drying apparatus and then sealed.

b) Preparation of the active drug suspension for parenteral administration (reconstitution)

To the contents of a vial containing 75 mg of lyophilized diclofenac sodium (preparation as described in a) above) are added, at room temperature, 2.0 ml of sterilized water for injection and the lyophilized drug is suspended by shaking. The suspension is withdrawn from the vial with a sterilized syringe and can be administered intramuscularly.

EXAMPLE 2 a) Following the procedure of Example 1a), it is possible to prepare lyophilized drug formulations containing 75 mg of diclofenac sodium and 100 mg of mannitol and 9 mg of NaCl. Alternatively, these lyophilized formulations may also additionally contain 0.01 to 10 mg of Synperonic ®.

b) Following the procedure of Example 1b), it is possible to suspend, at room temperature, lyophilized drug formulations containing 75 mg of diclofenac sodium in 2.0 ml of sterilized water for injection which contains 0.9% of NaCl, or lyophilized drug formulations containing 75 mg of diclofenac sodium and 100 mg of mannitol, or 75 mg of diclofenac sodium, 50 mg of mannitol and 9 mg of NaCl in 2.0 ml of sterilized water for injection. Alternatively, these lyophilized drug formulations can also be suspended with the addition of 0.01 to 10 mg of Synperonic ®. The isotonic suspensions so obtained can be withdrawn by a sterilized syringe and administered intramuscularly.

EXAMPLE 3 a) Preparation of the dry formulation (powder)

| Composition of each ampoule: | |
|---|---|
| diclofenac | 75 mg |
| lecithin (Epikuron ® 145, 170 or 200) | 2–20 mg |

Preparation of 10 ampoules:

The lecithin is dissolved in 10 ml of methylene chloride and the solution is filtered through a membrane (pore size: 0.2 μm). To the filtered solution are added 750 mg of micronised diclofenac sodium having an average particle size smaller than 20 μm, and the suspension so obtained is deagglomerated (q.v. Example 1a). The solvent is then removed under vacuum. The diclofenac sodium powder coated with lecithin is filled into vials such that each contains 75 mg of diclofenac sodium.

b) Preparation of the active drug suspension for parenteral administration

Following the procedure of Example 1a), the contents of a vial containing 75 mg of diclofenac sodium in the form of the lecithin-coated powder are suspended at room temperature in 2.0 ml of sterilized water for injection which contains 0.9% of NaCl or in 2.0 ml of sterilized water which contains an isotonic mixture of NaCl and mannitol.

EXAMPLE 4 a) Preparation of the lyophilized drug formulation

| Composition of each ampoule: | |
|---|---|
| diclofenac sodium | 75 mg |
| NaCl | 5.4 mg |
| mannitol | 20 mg |
| PLURONIC | 0.07 mg |

Preparation of 10 ampoules:

54.0 mg of sodium chloride (puriss.), 200 mg mannitol and 0.7 mg PLURONIC are dissolved in 7.0 ml of distilled water and the solution is filtered through a membrane filter (pore size: 0.2 μm) and sterilized, e.g. in an autoclave at ca. 120° C. The sterilized suspending agent is cooled to 5° C. To the cooled solution are added 750 mg of micronised diclofenac sodium (puriss.) having an average particle size smaller than 20 μm and the resultant suspension is deagglomerated, e.g. in a piston homogeniser or ultrasonics disintegrator. The crystalline suspension is filled at 5° C. into 10 sterilized vials of a volume suitable for 0.8 g substance. The vials are frozen at −45° C., lyophilized in a freeze drying apparatus and then sealed.

b) Preparation of the active drug suspension for parenteral administration (reconstitution)

To the contents of a vial containing 75 mg of lyophilized diclofenac sodium (preparation as described in a) above) are added, at room temperature, 1.0 ml of sterilized water for injection and the lyophilized drug is suspended by shaking. The suspension is withdrawn from the vial with a sterilized syringe and can be administered intramuscularly.

EXAMPLE 5 a) Preparation of the lyophilized drug formulation

| Composition of each ampoule: | |
|---|---|
| diclofenac sodium | 75 mg |
| mannitol | 40 mg |

Preparation of 10 ampoules:

400 mg mannitol (puriss.-free of pyrogens) are dissolved in 6 ml of distilled water and this solution is filtered through a membrane filter (pore size: 0.2 μm) and is sterilized in an autoclave at 120° C. The sterilized mannitol solution is cooled to 5° C. To the cooled solution are added 750 mg of micronised diclofenac sodium (puriss.) having an average particle size smaller than 20 μm. The resultant suspension is desagglomerated, e.g. in a piston homogeniser or ultrasonics disintegrator. The crystalline suspension is filled at 5° C. into 10 sterilized vials of a volume of 0.6 ml. The vials are frozen at −45° C., lyophilized in a freeze drying apparatus and then sealed.

b) Preparation of the active drug suspension for parenteral administration (reconstitution)

To the contents of a vial containing 75 mg of lyophilized diclofenac sodium (preparation as described in a) above) are added, at room temperature, 1.0 ml of sterilized water for injection and the lyophilized drug is suspended by shaking. The suspension is withdrawn from the vial with a sterilized syringe and can be administered intramuscularly.

We claim:

1. A suspension administrable to humans by intramuscular injection consisting essentially of:
   (a) 1–3 ml of sterile water; and
   (b) 25–150 mg of a sterile, lyophilized formulation of micronized diclofenac sodium and at least one pharmaceutically acceptable adjuvant for establishing isotonic conditions selected from the group consisting of sodium chloride, sorbitol, mannitol and glucose.

2. A process for the preparation of a suspension administrable to humans by intramuscular injection which process steps are consisting essentially of:
   (a) preparing a sterile, lyophilized formulation of diclofenac sodium in micronized crystal form and at least one pharmaceutically acceptable adjuvant for establishing isotonic conditions selected from the group consisting of sodium chloride, sorbitol, mannitol and glucose;
   (b) adding 1–3 ml of sterile water; and
   (c) suspending the lyophilized formulation.

* * * * *